United States Patent
Kahl et al.

(10) Patent No.: US 10,687,753 B2
(45) Date of Patent: Jun. 23, 2020

(54) SYSTEM AND METHOD FOR OPTIMIZING BODY AND OBJECT INTERACTIONS

(71) Applicant: 3M INNOVATIVE PROPERTIES COMPANY, St. Paul, MN (US)

(72) Inventors: Jonathan T. Kahl, Woodbury, MN (US); Nathan J. Anderson, Woodbury, MN (US); James J. Kobe, Newport, MN (US); Roger T. Hager, Minneapolis, MN (US); Thomas B. Galush, Roseville, MN (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 66 days.

(21) Appl. No.: 15/763,267

(22) PCT Filed: Sep. 26, 2016

(86) PCT No.: PCT/US2016/053671
§ 371 (c)(1),
(2) Date: Mar. 26, 2018

(87) PCT Pub. No.: WO2017/058700
PCT Pub. Date: Apr. 6, 2017

(65) Prior Publication Data
US 2018/0303399 A1    Oct. 25, 2018

Related U.S. Application Data (60) Provisional application No. 62/234,857, filed on Sep. 30, 2015.

(51) Int. Cl.
*A61B 5/22*    (2006.01)
*A61B 5/00*    (2006.01)
(Continued)

(52) U.S. Cl.
CPC .............. *A61B 5/225* (2013.01); *A61B 5/742* (2013.01); *G01L 5/008* (2013.01); *G01N 19/02* (2013.01);
(Continued)

(58) Field of Classification Search
CPC ......... G01L 5/228; G01L 5/226; G01L 5/008; G01L 1/205; G01N 19/02; A61B 5/225;
(Continued)

(56) References Cited

U.S. PATENT DOCUMENTS 5,542,676 A    8/1996    Howe, Jr.
5,681,993 A    10/1997    Heitman
(Continued)

FOREIGN PATENT DOCUMENTS

JP    H09-201208 A    8/1997
JP    2001-330526    11/2001
(Continued)

OTHER PUBLICATIONS

Cutkosky et al. "Skin Materials for Robotic Fingers", Proceedings. 1987 IEEE International Conference on Robotics and Automation, Mar. 31-Apr. 3, 1987. (Year: 1987).*
(Continued)

*Primary Examiner* — Jonathan M Dunlap
(74) *Attorney, Agent, or Firm* — Yufeng Dong (57) ABSTRACT

Systems and methods for optimizing body and object interactions are provided. Based on obtained contact pressure maps and coefficient of friction (COF) maps at a contact interface where at least a portion of a body is in physical contact with a surface of an object, friction force maps can be determined, which can be used to optimize body and object interactions.

12 Claims, 5 Drawing Sheets

(51) Int. Cl.
*G01L 5/00* (2006.01)
*G01N 19/02* (2006.01)

(52) U.S. Cl.
CPC ..... *A61B 5/7246* (2013.01); *A61B 2562/0247* (2013.01); *A61B 2562/046* (2013.01); *G05B 2219/39505* (2013.01); *G05B 2219/39542* (2013.01); *G05B 2219/39546* (2013.01); *G05B 2219/40567* (2013.01)

(58) Field of Classification Search
CPC ............... A61B 5/7246; A61B 5/742; A61B 2562/0247; A61B 2562/046; G05B 2219/39505; G05B 2219/40567; G05B 2219/39542; G05B 2219/39546
See application file for complete search history.

(56) References Cited

U.S. PATENT DOCUMENTS

| | | | | |
|---|---|---|---|---|
| 6,388,655 | B1* | 5/2002 | Leung | G01L 1/20 341/34 |
| 6,813,949 | B2* | 11/2004 | Masaniello | F17D 5/02 73/602 |
| 7,584,645 | B2* | 9/2009 | David | G01N 19/02 702/41 |
| 7,631,557 | B2 | 12/2009 | DeBeliso | |
| 7,707,001 | B2* | 4/2010 | Obinata | B25J 13/082 356/32 |
| 7,878,075 | B2* | 2/2011 | Johansson | B25J 13/084 73/862.046 |
| 8,181,540 | B2* | 5/2012 | Loeb | G01L 5/228 73/645 |
| 8,272,278 | B2* | 9/2012 | Loeb | G01L 5/228 374/45 |
| 8,644,986 | B2* | 2/2014 | Tsuboi | G05B 13/021 414/1 |
| 9,221,171 | B2* | 12/2015 | Sugiura | G01B 17/00 |
| 9,434,479 | B2* | 9/2016 | Metzger, Jr. | B60T 8/1703 |
| 9,605,952 | B2* | 3/2017 | Rose | G01L 1/16 |
| 9,649,764 | B1* | 5/2017 | Sun | B25J 9/1612 |
| 2004/0031337 | A1* | 2/2004 | Masaniello | F17D 5/02 73/865.8 |
| 2005/0141456 | A1 | 8/2005 | Hirschman et al. | |
| 2006/0012198 | A1* | 1/2006 | Hager | B25J 9/1612 294/106 |
| 2006/0169023 | A1 | 8/2006 | David | |
| 2008/0077361 | A1* | 3/2008 | Boyd | B25J 9/1612 702/189 |
| 2008/0087069 | A1* | 4/2008 | Renken | G01L 9/0073 73/1.63 |
| 2008/0087105 | A1* | 4/2008 | Renken | G01L 1/148 73/862.68 |
| 2009/0025475 | A1 | 1/2009 | DeBeliso | |
| 2009/0076657 | A1* | 3/2009 | Tsuboi | G05B 13/021 700/275 |
| 2009/0133508 | A1* | 5/2009 | Johansson | B25J 13/084 73/862.046 |
| 2009/0272201 | A1* | 11/2009 | Loeb | G01L 5/228 73/862.041 |
| 2010/0139418 | A1* | 6/2010 | Loeb | G01L 5/228 73/862.046 |
| 2010/0274447 | A1 | 10/2010 | Stumpf | |
| 2014/0214209 | A1* | 7/2014 | Sugiura | G01B 17/00 700/259 |
| 2015/0019013 | A1* | 1/2015 | Rose | G01L 1/16 700/258 |
| 2016/0066634 | A1* | 3/2016 | Ray | A41D 19/01547 2/163 |
| 2019/0113440 | A1* | 4/2019 | Koike | G01M 17/022 |

FOREIGN PATENT DOCUMENTS

| | | |
|---|---|---|
| JP | 2003-057134 | 2/2003 |
| KR | 10-1302441 | 9/2013 |
| WO | 2012-154012 | 11/2012 |

OTHER PUBLICATIONS

Tiezzi et al. "Effect of Layer Compliance on Frictional Behavior of Soft Robotic Fingers", 2006 IEEE/RSJ International Conference on Intelligent Robots and Systems, Oct. 9-15, 2006. (Year: 2006).*

Bernard, Musculoskeletal Disorders and Workplace Factors, National Institute for Occupational Safety and Health (NIOSH). U.S. Department of Health and Human Services, Jul. 1997, Chapter 5, 131 pages.

Harih, "Tool-Handle Design Based on a Digital Human Hand Model," International Journal of Industrial Ergonomics, 2013, vol. 43, pp. 288-295.

Hendrick, "Multi-Sensor Based Segmentation of Human Manipulation Tasks," 2010 IEEE International Conference on Multisensor Fusion and Integration for Intelligent Systems, University of Utah, Salt Lake City, UT, USA, Sep. 2010, pp. 223-229.

International Search Report for PCT International Application No. PCT/US2016/053671, dated Jan. 5, 2017, 3 pages.

* cited by examiner

SYSTEM AND METHOD FOR OPTIMIZING BODY AND OBJECT INTERACTIONS

CROSS REFERENCE TO RELATED APPLICATIONS

This application is a national stage filing under 35 U.S.C. 371 of PCT/US2016/053671, filed Sep. 26, 2016, which claims the benefit of U.S. Application No. 62/234,857 filed Sep. 30, 2015 the disclosure of which is incorporated by reference in its/their entirety herein.

TECHNICAL FIELD

The present disclosure relates to systems and methods for optimizing body and object interactions, in particular, through the utilization of contact interface mapping.

BACKGROUND

The force required for body-object interactions, e.g., by a hand for gripping tasks, may determine the degree of fatigue, performance, and the probability of developing musculoskeletal disorders. An ergonomic design of body-object interfaces can reduce the risk of musculoskeletal disorders. For example, handle and/or glove modifications that selectively enhance friction at key regions of the hand and object interface can reduce the grip force required to perform a task. A grip force transducer and grip force assessment system and method were described in U.S. Patent Pub. No. 2009/0025475 (DeBeliso et al.).

SUMMARY

There is a desire to optimizing body-object interactions, especially for body-object interfaces where a contact force is not equally distributed and an effectively implement of Amonton's law of friction may be challenging. The present disclosure provides systems and methods for optimizing body-object interactions, for example, body and object interactions through the utilization of contact pressure maps and coefficient of friction (COF) maps. For example, in some embodiments, a hand pressure map can be combined with a COF map of material(s) of a glove to obtain desired information.

In one aspect, a method includes obtaining a contact pressure map at a contact interface where at least a portion of a body is in physical contact with a surface of an object. The contact pressure map is a first representation of the contact interface. The method further includes obtaining a coefficient of friction map at the contact interface. The coefficient of friction map is a second representation of the contact interface. The method further includes calculating a friction force map based on the obtained contact pressure map and the obtained coefficient of friction map. The friction force map is a third representation of the contact interface as a function of the first and second representations.

In another aspect, a method includes obtaining a hand pressure map at a contact interface where at least a portion of a palm side of the hand is in physical contact with the object. The hand pressure map is a first representation of the palmar view of the hand. The method further includes obtaining a coefficient of friction map at the contact interface. The coefficient of friction map is a second representation of palmar view of the hand. The method further includes calculating a friction force map based on the obtained hand pressure map and the obtained coefficient of friction map. The friction force map is a third representation of palmar view of the hand as a function of the first and second representations. In some embodiments, the method is for designing a glove that is used for a hand to handle an object.

Various unexpected results and advantages are obtained in exemplary embodiments of the disclosure. One such advantage of exemplary embodiments of the present disclosure is that through the use of body-object contact pressure mapping and input metrics of the material(s), tasks, and geometric characteristics of object(s) and individual(s), friction force maps at the contact interface can be produced and used for optimizing body-object interfaces or interactions in terms of human performance and perceptual metrics including, for example, performance, comfort, fatigue, vibration transference, etc. Objects described herein can include, for example, body worn articles and accessories, personal protective equipment, athletic equipment, military equipment, tools, and devices. A body of a portion of a body to be contacted with the objects can be, for example, head, face, torso, arms, hands, legs, and feet.

LIST OF EXEMPLARY EMBODIMENTS

Exemplary embodiments are listed below. It is to be understood that any one of embodiments 1-17, 18-32, and 33-35 can be combined.

Embodiment 1 is a method comprising:
  obtaining a contact pressure map at a contact interface where at least a portion of a body is in physical contact with a surface of an object, the contact pressure map being a first representation of the contact interface;
  obtaining a coefficient of friction map at the contact interface, the coefficient of friction map being a second representation of the contact interface; and
  calculating, via a processor, a friction force map based on the obtained contact pressure map and the obtained coefficient of friction map, the friction force map being a third representation of the contact interface as a function of the first and second representations.

Embodiment 2 is the method of embodiment 1, wherein obtaining the contact pressure map comprises positioning a plurality of sensors at locations on the contact interface, and measuring a set of contact pressure values at the locations.

Embodiment 3 is the method of embodiment 2, wherein obtaining the contact pressure map further comprises converting the set of contact pressure values to the first representation of the contact interface.

Embodiment 4 is the method of any one of embodiments 1-3, wherein the contact pressure map is a statistical contact pressure map based on a plurality of contact pressure maps.

Embodiment 5 is the method of any one of embodiments 1-4, wherein obtaining the coefficient of friction map comprises measuring coefficient of friction for one or more materials at the contact interface.

Embodiment 6 is the method of embodiment 5, wherein the coefficient of friction is a statistical coefficient of friction under a plurality of surface type conditions.

Embodiment 7 is the method of embodiment 6, wherein the plurality of surface type conditions include dry, wet, chalky, and oily conditions.

Embodiment 8 is the method of any one of embodiments 1-7, wherein obtaining the coefficient of friction map comprises inputting the coefficient of friction for the materials from a database.

Embodiment 9 is the method of any one of embodiments 1-8, wherein the third representation is obtained by multiplying the first and second representations.

Embodiment 10 is the method of any one of embodiments 1-9, further comprising comparing the calculated friction force map to predetermined criteria.

Embodiment 11 is the method of embodiment 10, further comprising adjusting the contact interface based on the comparison.

Embodiment 12 is the method of embodiment 11, wherein adjusting the contact interface comprises adjusting one or more materials at the contact interface.

Embodiment 13 is the method of embodiment 12, wherein adjusting the materials comprises adjusting the distribution of the materials.

Embodiment 14 is the method of embodiment 12 or 13, wherein adjusting the materials comprises changing at least one of the materials to a different material.

Embodiment 15 is the method of any one of embodiments 11-14, adjusting the contact interface comprises adjusting a surface profile at the contact interface.

Embodiment 16 is the method of any one of embodiments 1-5, wherein the object includes one or more of body worn articles and accessories, personal protective equipment, athletic equipment, military equipment, tools, and devices.

Embodiment 17 is the method of any one of embodiments 1-6, wherein the body includes at least a portion of a head, a face, a torso, an arm, a hand, a leg, and a foot.

Embodiment 18 is a method comprising:
obtaining a hand pressure map at a contact interface where at least a portion of a palm side of the hand is in physical contact with the object, the hand pressure map being a first representation of palmar view of the hand;
obtaining a coefficient of friction map at the contact interface, and the coefficient of friction map being a second representation of palmar view of the hand; and
calculating, via a processor, a friction force map based on the obtained hand pressure map and the obtained coefficient of friction map, the friction force map being a third representation of palmar view of the hand as a function of the first and second representations.

Embodiment 19 is the method of embodiment 18, wherein obtaining the hand pressure map comprises positioning a plurality of sensors at locations on the contact interface, and measuring a set of contact pressure values at the locations.

Embodiment 20 is the method of embodiment 19, wherein obtaining the contact pressure map further comprises converting the set of contact pressure values to the first representation of the contact interface.

Embodiment 21 is the method of any one of embodiments 18-20, wherein the hand pressure map is a statistical hand pressure map based on a plurality of hand pressure maps.

Embodiment 22 is the method of any one of embodiments 18-21, wherein obtaining the coefficient of friction map comprises measuring coefficient of friction for one or more materials on the inner or outer surface of the palm side of the glove.

Embodiment 23 is the method of embodiment 22, wherein the coefficient of friction is a statistical coefficient of friction under a plurality of surface type conditions.

Embodiment 24 is the method of embodiment 23, wherein the plurality of surface type conditions include dry, wet, chalky, and oily conditions.

Embodiment 25 is the method of any one of embodiments 18-24, wherein obtaining the coefficient of friction map comprises inputting the coefficient of friction for the materials from a database.

Embodiment 26 is the method of any one of embodiments 18-25, wherein the third representation is obtained by multiplying the first and second representations.

Embodiment 27 is the method of any one of embodiments 18-26, further comprising comparing the calculated friction force map to predetermined criteria.

Embodiment 28 is the method of embodiment 27, further comprising adjusting the contact interface based on the comparison.

Embodiment 29 is the method of embodiment 28, wherein adjusting the contact interface comprises adjusting one or more materials of the inner or outer surface of the palm side of the glove.

Embodiment 30 is the method of embodiment 29, wherein adjusting the materials comprises adjusting the distribution of the materials.

Embodiment 31 is the method of embodiment 29 or 30, wherein adjusting the materials comprises changing at least one of the materials to a different material.

Embodiment 32 is the method of any one of embodiments 28-31, wherein adjusting the contact interface comprises adjusting a surface profile at the contact interface.

Embodiment 33 is a system comprising:
a pressure measurement component comprising a plurality of sensors at locations on a contact interface configured to measure an array of contact pressure values at the contact interface where at least a portion of a body is in physical contact with a surface of an object, the contact pressure map being a first representation of the contact interface;
a computation component functionally connected to the pressure measurement, configured to receive signals related to the array of contact pressure values from the pressure measurement component, and obtain a contact pressure map based on the received signals,
wherein the computation component is further configured to obtain a coefficient of friction map at the contact interface, the coefficient of friction map being a second representation of the contact interface, and
wherein the computation component includes a processor, the processor is configured to calculate a friction force map based on the obtained contact pressure map and the obtained coefficient of friction map, the friction force map being a third representation of the contact interface as a function of the first and second representations.

Embodiment 34 is the system of embodiment 33, further comprises a second measurement component configured to measure coefficient of friction for one or more materials at the contact interface.

Embodiment 35 is the system of embodiment 33 or 34, wherein the coefficient of friction map is obtained by inputting coefficient of friction for one or more materials at the contact interface from a database.

Various aspects and advantages of exemplary embodiments of the disclosure have been summarized. The above Summary is not intended to describe each illustrated embodiment or every implementation of the present certain exemplary embodiments of the present disclosure. The Drawings and the Detailed Description that follow more particularly exemplify certain preferred embodiments using the principles disclosed herein.

BRIEF DESCRIPTION OF THE DRAWINGS

The disclosure may be more completely understood in consideration of the following detailed description of various embodiments of the disclosure in connection with the accompanying figures, in which.

In the drawings, like reference numerals indicate like elements. While the above-identified drawing, which may not be drawn to scale, sets forth various embodiments of the present disclosure, other embodiments are also contemplated, as noted in the Detailed Description. In all cases, this disclosure describes the presently disclosed disclosure by way of representation of exemplary embodiments and not by express limitations. It should be understood that numerous other modifications and embodiments can be devised by those skilled in the art, which fall within the scope and spirit of this disclosure.

DETAILED DESCRIPTION

The present disclosure provide systems and methods for optimizing body-object interactions, for example, body-object interactions through the utilization of body-object contact pressure maps and coefficient of friction (COF) maps at contact interfaces. For example, in some embodiments, a hand pressure map can be combined with a COF map of material(s) of a glove to obtain desired information. Objects described herein can include, for example, body worn articles and accessories, personal protective equipment, athletic equipment, military equipment, tools, and devices. A body of a portion of a body to be contacted with the objects can be, for example, head, face, torso, arms, hands, legs, and feet.

Figure 1A:
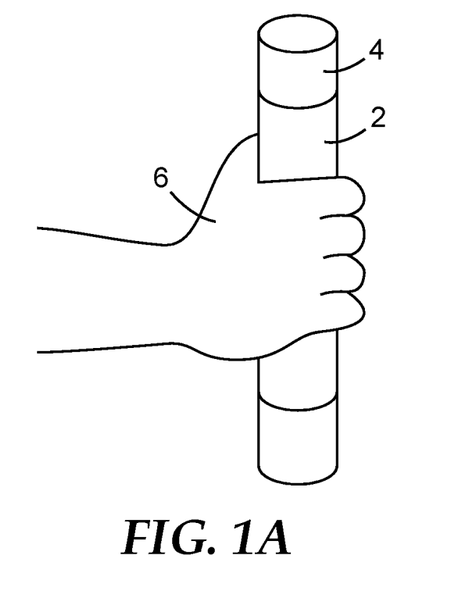
FIG. 1A illustrates a perspective side view of a hand pressure measurement device, according to one embodiment.
Figure 1B:
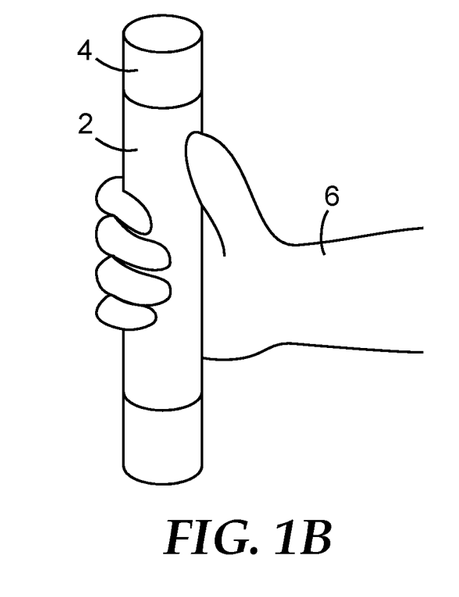
FIG. 1B illustrates another perspective side view of the hand pressure measurement device of FIG. 1A.
Figure 2A:
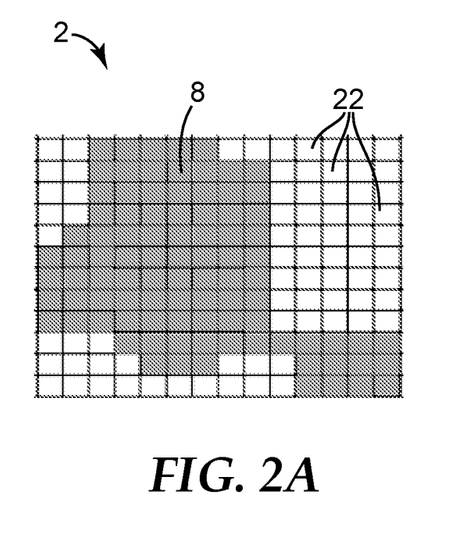
FIG. 2A illustrates an array of hand pressures measured by the hand pressure measurement device of FIGS. 1A-B, according to one embodiment.
Figure 2B:
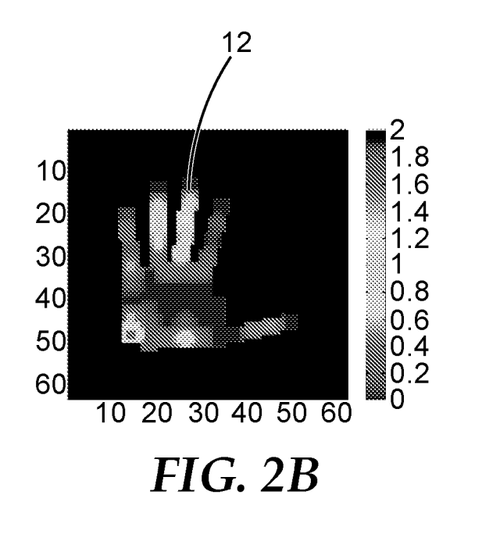
FIG. 2B illustrates a first representation of palmar view of a hand according to the array of hand pressures of FIG. 2A.

FIGS. 1A-B and 2A-B illustrate how to measure a hand pressure map at hand-object contact interfaces. A pressure pad 2 is fixed about a cylinder 4. The pressure pad 2 includes an array of pressure sensors 22 (see FIG. 2A). When a hand 6 is in physical contact with the pressure pad 2, e.g., gripping the cylinder 4, a distribution 8 of contact pressure values at the contact interface can be measured by the array of pressure sensors 22 of the pressure pad 2, as shown in FIG. 2A. The distribution 8 of contact pressure values as measured by the pressure pad 2 can be converted to a 2D representation 12 of palmar view of the hand 6, as shown in FIG. 2B. Such conversion can be performed by, for example, assigning each of the pressure sensors 22 of FIG. 2A to the respective locations on the palmar view of the hand 6. In the depicted embodiment, the 2D representation 12 can serve as a 2D hand pressure map, which may display varying contact pressure values at different locations of the palm side of the hand. The 2D representation 12 can be expressed as $P(x_i, y_i)$ where $(x_i, y_i)$ denotes surface locations of the palm side of the hand in a 2D Cartesian x-y coordinate system, and $P(x_i, y_i)$ denotes the respective measured hand pressure values on the surface locations. In some embodiments, a hand pressure map can be a 3D representation of palmar view of a hand, for example, a distribution of contact pressure values on a 3D surface of palm side of a hand. The 3D representation can be expressed as $P(x_i, y_i, z_i)$ where $(x_i, y_i, z_i)$ denotes surface locations of the palm side of the hand in a 3D Cartesian coordinates system.

The array of pressure sensors 22 can be positioned at any suitable locations at a contact interface. In some embodiments, the hand pressure map can be measured with the hand 6 with a glove, and the array of pressure sensors 22 can be positioned at a contact interface between the glove and the cylinder 4. In some embodiments, the array of pressure sensor 22 can be positioned at a contact interface between an inner surface of the glove and the palm side of the hand 6.

In some embodiments, the hand pressure map may be a statistical hand pressure map based on multiple measured hand pressure maps. The hand pressure maps can be measured, for example, for multiple hands of a group of participants, for multiple tools or objects having various shapes and/or surface conditions, for multiple tasks with various hand-tool interactions (e.g., a torque task, a pull task, etc.), or under various surface type conditions (e.g., dry, wet, chalky, oily conditions, etc.). The statistical hand pressure map can be obtained based on a statistical analysis, for example, a mean, a weighted sum, etc., of the measured multiple maps.

Figure 3A:
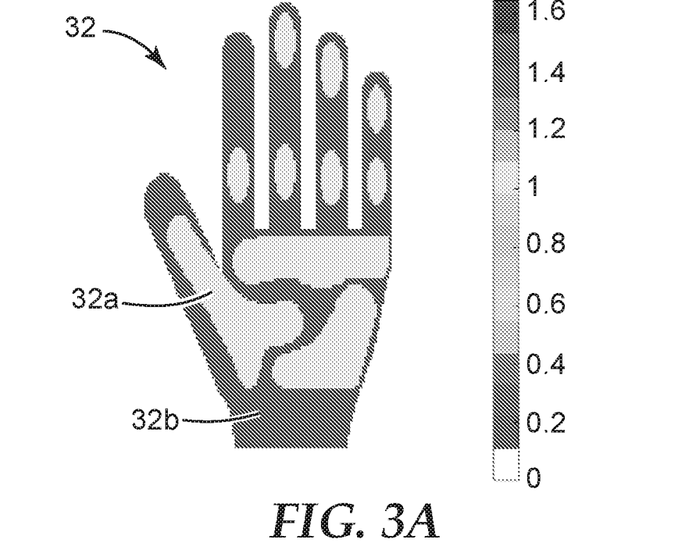
FIG. 3A illustrates a second representation of palmar view of a hand according to a coefficient friction map of an outer palm side of a glove, according to one embodiment.
Figure 3B:
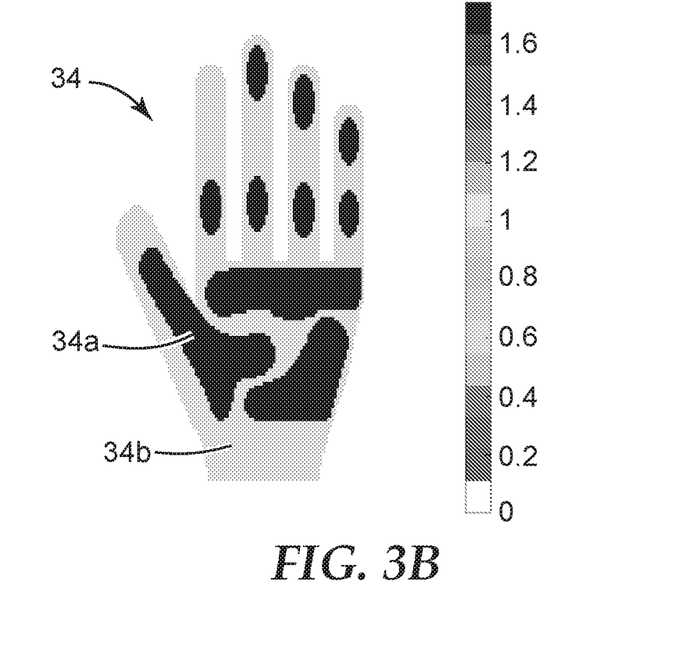
FIG. 3B illustrates a second representation of palmar view of a hand according to a coefficient friction map of an inner palm side of the glove of FIG. 3A, according to one embodiment.

FIGS. 3A-B illustrates coefficient of friction (COF) maps 32 and 34 for an outer surface and an inner surface of the palm side of a glove, respectively, according to one embodiment. The outer surface of the glove may be made of one or more materials including, for example, leather, gripping materials from 3M Company, St. Paul, etc. The materials may attribute to different coefficient of friction values at respective locations on a contact interface between the outer surface of the glove and an object such as a tool. The COF map 32 in FIG. 3A can be a second representation of palm view of the hand, and corresponds to a distribution of material(s) on the outer surface of the glove. In the depicted embodiment, the outer surface is made of a first material in areas 32a and a second material in areas 32b. The areas 32a and 32b have different COF values. It is to be understood that the outer surface of the glove can be made of one, or more than two kinds of materials having different COF values. Similarly, the inner surface may be made of one or more materials including, for example, leather, gripping materials, etc. The materials may attribute to different coefficient of friction values at respective locations on a contact interface between the inner surface of the glove and the palm side of the hand. The COF map 34 in FIG. 3B can be a second representation of palm view of the hand, and corresponds to a distribution of material(s) on the inner surface of the glove. In the depicted embodiment, the inner surface is made of a first material in areas 34a and a second material in areas 34b. The areas 34a and 34b have different COF values. It is to be understood that the outer surface of the glove can be made of one, or more than two kinds of materials having different COF values.

The 2D representations 32 and 34 of FIG. 3A-B can be expressed as $COF(x_i, y_i)$ where $(x_i, y_i)$ denotes surface locations of the palm side of the hand in a 2D Cartesian x-y coordinate system, and $COF(x_i, y_i)$ denotes the respective coefficient of friction values for the materials on the outer or inner surface of the palm side of the glove. In some embodiments, a COF map can be a 3D representation of palmar view of a hand, for example, a distribution of COF values on a 3D surface of palm side of a hand. The 3D representation can be expressed as $COF(x_i, y_i, z_i)$ where $(x_i, y_i, z_i)$ denotes surface locations of the palm side of the hand in a 3D Cartesian coordinate x-y-z system.

In some embodiments, coefficient of friction of materials can be measured by suitable instruments under various surface type conditions including, for example, dry, wet, chalky, oily conditions, etc. The coefficient of friction of a specific material can be a statistical coefficient of friction under the various surface type conditions. The measured coefficient of friction values may vary, for example, in the range from about 0.01 to 10 under various surface type conditions. In some embodiments, the coefficient of friction can be obtained by taking the mean coefficient of friction values for each surface type conditions. It is to be understood that in some embodiments, coefficient of friction of materials may be known and can be imported from a database.

A friction force map can be obtained based on the obtained hand pressure map and COF map such as shown in FIGS. 2B and 3A-B. The friction force map can serve as a third representation of palmar view of the hand as a function of the first and second representations of palmar view of the hand. In some embodiments, the friction force map is a 2D representation that can be expressed as $F(x_i, y_i)$ where $(x_i, y_i)$ denotes surface locations of the palm side of the hand in a 2D Cartesian x-y coordinate system, and $F(x_i, y_i)$ denotes the respective friction force values on the outer or inner surface of the palm side of the glove. $F(x_i, y_i)$ can be obtained, for example, by multiplying $P(x_i, y_i)$ and $COF(x_i, y_i)$. In some embodiments, a friction force map can be a 3D representation of palmar view of a hand, for example, a distribution of friction force values on a 3D surface of palm side of a hand. The 3D representation can be expressed as $F(x_i, y_i, z_i)$ that can be obtained, for example, by multiplying $P(x_i, y_i, z_i)$ and $COF(x_i, y_i, z_i)$.

In some embodiments, a statistical friction force value (e.g., a mean friction force value) can be obtained based on the friction force map for each of a group of gloves under test. A linear regression can be performed on the mean friction force value and the corresponding performance metric (e.g., a maximum pull test) for each of the gloves. This provides a simple and effective way of applying the friction force maps to reliably predict performance of gloves on a specific task (e.g., a pull task).

Figure 4A:
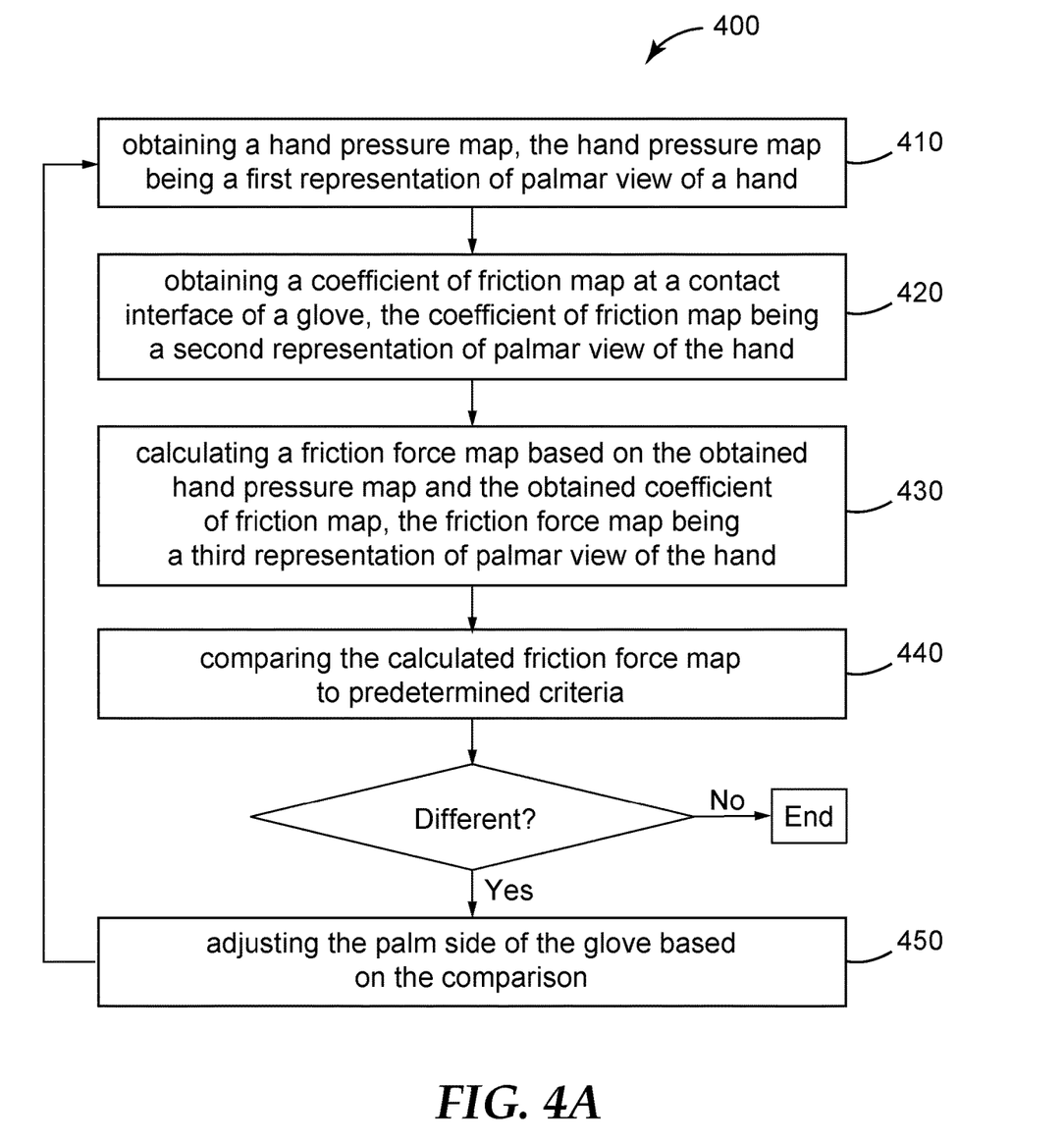
FIG. 4A is a flow diagram of a method for optimizing a glove, according to one embodiment.

FIG. 4A illustrates a flow diagram of a method 400 for optimizing hand, glove and object interactions. At 410, a hand pressure map is obtained, for example, when at least a portion of palm side of a hand is in physical contact with an object such as a tool. The hand pressure map is a first representation of palmar view of a hand. In some embodiments, the hand pressure map can be obtained by positioning an array of sensors at locations on a contact interface, and measuring a set of contact pressure values at the locations. The contact interface can be, for example, between an inner surface of a glove and the palm side of the hand that are in physical contact, between an outer surface of a glove and an object that are in physical contact, or between the palm side of the hand and an object that are in physical contact. FIGS. 1A-B illustrates measuring a set of contact pressure values via the pressure pad 2 including an array of pressure sensors. The set of contact pressure values can be converted to a first representation of palmar view of the hand such as, for example, shown in FIG. 2B. The method 400 then proceeds to 420.

At 420, a coefficient of friction map at a contact interface of the glove is obtained. The COF map is a second representation of palmar view of the hand. In some embodiments, the coefficient of friction map can be obtained by measuring coefficient of friction for one or more materials on the inner or outer surface of the palm side of the glove such as, for example, shown in FIGS. 3A and 3B. In some embodiments, the coefficient of friction for a specific material may be a statistical coefficient of friction of the material measured under multiple surface type conditions including, for example, dry, wet, chalky, and oily conditions. The statistical COF map can be obtained based on a statistical analysis of the measured multiple maps, for example, a mean, a weighted sum, etc. In some embodiments, the coefficient of friction map may be obtained by inputting coefficient of friction values for the materials from a database. The method 400 then proceeds to 430.

At 430, a friction force map is calculated based on the obtained hand pressure map and the obtained coefficient of friction map. The friction force map is a third representation of palmar view of the hand as a function of the first and second representations. In some embodiments, the friction force map can be a 2D representation expressed as $F(x_i, y_i)$ where $(x_i, y_i)$ denotes surface locations of the palm side of the hand in a 2D Cartesian x-y coordinate system, and $F(x_i, y_i)$ denotes the respective friction force values for the materials on the outer or inner surface of the glove, can be calculated by multiplying the respective $P(x_i, y_i)$ and $COF(x_i, y_i)$. In some embodiments, the friction force map can be a 3D representation expressed as $F(x_i, y_i, z_i)$ where $(x_i, y_i, z_i)$ denotes surface locations of the palm side of the hand in a 3D Cartesian x-y-z coordinate system, and $F(x_i, y_i, z_i)$ denotes the respective friction force values for the materials on the outer or inner surface of the glove, can be calculated by multiplying the respective $P(x_i, y_i, z_i)$ and $COF(x_i, y_i, z_i)$. The method 400 then proceeds to 440.

At 440, the calculated friction force map is compared to predetermined criteria. The predetermined criteria can be, for example, industrial standards including minimum/maximum friction forces desired for certain applications, a desired friction force map satisfying certain levels of human performance, comfort, fatigue, safety, vibration transference, etc. If the calculated friction force map does not satisfy the predetermined criteria, the method 400 proceeds to 460. If the calculated friction force map satisfies the predetermined criteria, the method 400 ends.

In some embodiments, metrics associated with the calculated friction force map can be used with a user's performance data and perception data to model metrics associated with the user's performance, comfort, fatigue, and/or vibration transference. The models associated with the friction force map can be used to reliably predict, for example, aspects of human performance and perception. For example, by modeling how hand pressure maps and material coefficient of friction maps affect various measures of human performance and perception (e.g., torque, comfort, pain, vibration transference, etc.), products and materials suitable for various applications can be optimized. Properties of the material that would be required to achieve a desired human performance metric can be determined.

At 460, the palm side of the glove is adjusted based on the comparison at 440. In some embodiments, the materials of inner or outer surface of the palm side of the glove can be adjusted, including, for example, adjusting the distribution of the materials, changing at least one of the materials to a different material, adjusting a surface profile of the palm side of the glove by varying layer thicknesses, adding a padding layer, etc. After adjusting the glove, the method 400 proceeds back to 410 where a new hand pressure map can be obtained based on the adjustment.

As described above, hand pressure maps, coefficient of friction maps, and the corresponding friction force maps at the contact interface can be obtained by reflecting various measures of human performance (e.g., torque, comfort, pain, vibration transference, etc.). While embodiments described above provide examples for hand-object interactions, it can be applied to other bodies (e.g., a face, a finger, a leg, a torso, a head, a hand, a foot, etc.) and objects (e.g., body worn articles and accessories, personal protective equipment, athletic equipment, military equipment, tools, and devices such as respiratory mask, eyewear, safety harness fit, etc.)

Figure 4B:
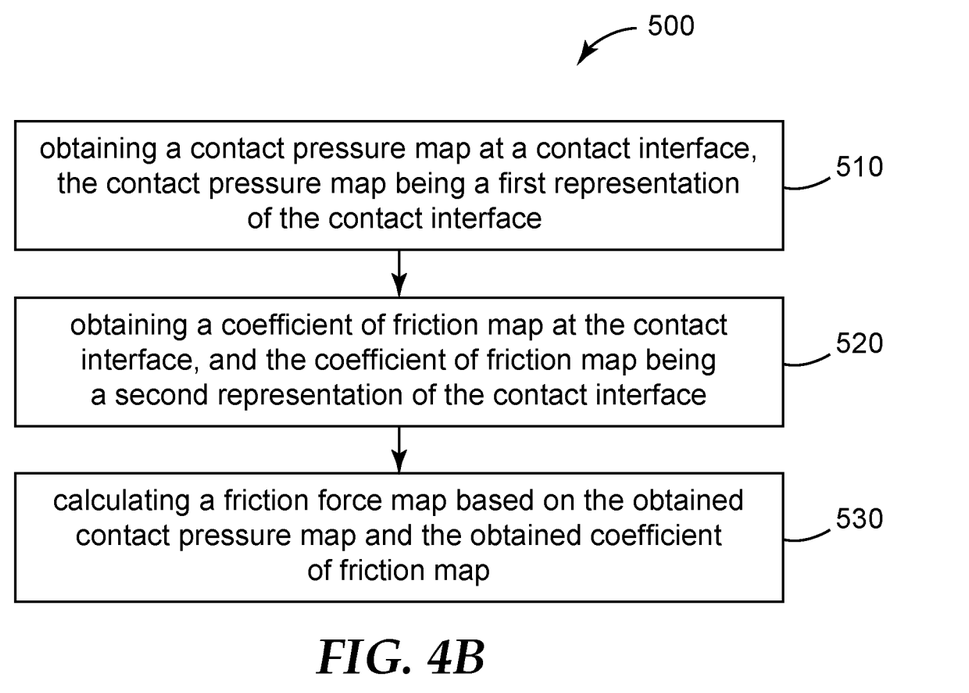
FIG. 4B is a flow diagram of a method for optimizing body-object interactions, according to one embodiment.

FIG. 4B illustrates a flow diagram of a method 500 for optimizing body and object interactions. At 510, a contact pressure map is obtained at a contact interface where a portion of a body is in physical contact with a surface of an object. In some embodiments, the contact pressure map can be measured at a contact interface between a body (e.g., a face, a finger, a leg, a torso, a head, a hand, a foot, etc.) and an object (e.g., body worn articles and accessories, personal protective equipment, athletic equipment, military equipment, tools, and devices such as respiratory mask, eyewear, safety harness fit, etc.) In some embodiments, the contact pressure map can be, for example, a hand pressure map that is measured when at least a portion of palm side of a hand is in physical contact with a tool. The contact pressure map is a first representation of the contact interface. In some embodiments, the contact pressure map can be obtained by positioning an array of sensors at locations on the contact interface, and measuring a set of contact pressure values at the locations which can be converted to a 2D or 3D contact pressure map. FIGS. 1A-B illustrates measuring a set of contact pressure values via the pressure pad 2 including an array of pressure sensors. The set of contact pressure values can be converted to a first representation of the contact interface, for example, shown in FIG. 2B. The method 500 then proceeds to 520.

At 520, a coefficient of friction (COF) map at the contact interface is obtained. The COF map is a second representation of the contact interface. In some embodiments, the coefficient of friction map can be obtained by measuring coefficient of friction for one or more materials on the surface of the object such as, for example, the inner or outer surface of the palm side of a glove as shown in FIGS. 3A and 3B. In some embodiments, the coefficient of friction for a specific material may be a statistical coefficient of friction of the material measured under multiple surface type conditions including, for example, dry, wet, chalky, and oily conditions. The statistical COF map can be obtained based on a statistical analysis of the measured multiple maps, for example, a mean, a weighted sum, etc. In some embodiments, the coefficient of friction map may be obtained by inputting coefficient of friction values for the materials from a database. The method 500 then proceeds to 530.

At 530, a friction force map is calculated based on the obtained contact pressure map and the obtained coefficient of friction (COF) map. The friction force map is a third representation of the contact interface as a function of the first and second representations obtained at 510 and 520. In some embodiments, the friction force map can be a 2D representation expressed as $F(x_i, y_i)$ where $(x_i, y_i)$ denotes locations at the contact interface in a 2D Cartesian x-y coordinate system, and $F(x_i, y_i)$ denotes the respective friction force values for the materials on the surface of the object that is in physical contact with the body. $F(x_i, y_i)$ can be calculated by multiplying the respective $P(x_i, y_i)$ and $COF(x_i, y_i)$. In some embodiments, the friction force map can be a 3D representation expressed as $F(x_i, y_i, z_i)$ where $(x_i, y_i, z_i)$ denotes locations at the contact interface in a 3D Cartesian x-y-z coordinate system, and $F(x_i, y_i, z_i)$ denotes the respective friction force values for the materials on the surface of the object. $F(x_i, y_i, z_i)$ can be calculated by multiplying the respective $P(x_i, y_i, z_i)$ and $COF(x_i, y_i, z_i)$.

The obtained friction force map can be used for various applications. In some embodiments, the friction force map can be compared to predetermined criteria. The predetermined criteria can be, for example, industrial standards including minimum/maximum friction forces desired for certain applications, a desired friction force map satisfying certain levels of human performance, comfort, fatigue, safety, vibration transference, etc. If the friction force map does not satisfy the predetermined criteria, the contact interface can be adjusted based on comparison in order to optimize body-object interactions. For example, in some embodiments, the surface of the object can be adjusted including, for example, adjusting the surface materials (e.g., adjusting the distribution of the materials, changing at least one of the materials to a different material, etc.), or adjusting a geometric characteristic of the object (e.g., changing the surface profile, varying layer thicknesses, adding a padding layer, etc). After adjusting the contact interface, a new contact pressure map and COF map can be obtained to update the friction force map.

In some embodiments, the obtained friction force map can be used to determine whether an object (e.g., a glove, a vest, a respirator, or a tool) is suitable to a body (e.g., a hand, a face, a finger, a leg, or a torso) of a specific user.

Figure 5A:
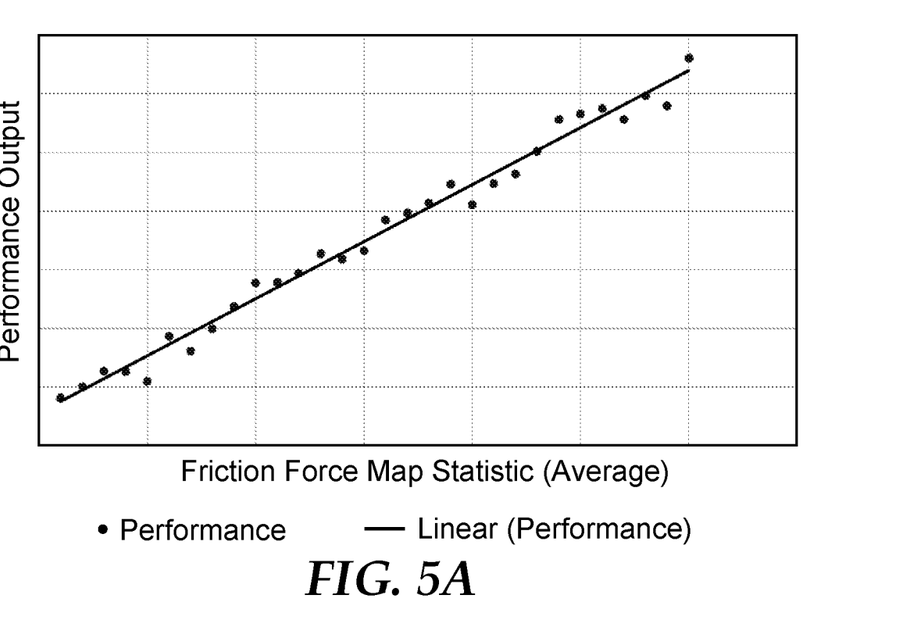
FIG. 5A illustrates the relationship between a friction force map and performance, according to one embodiment.
Figure 5B:
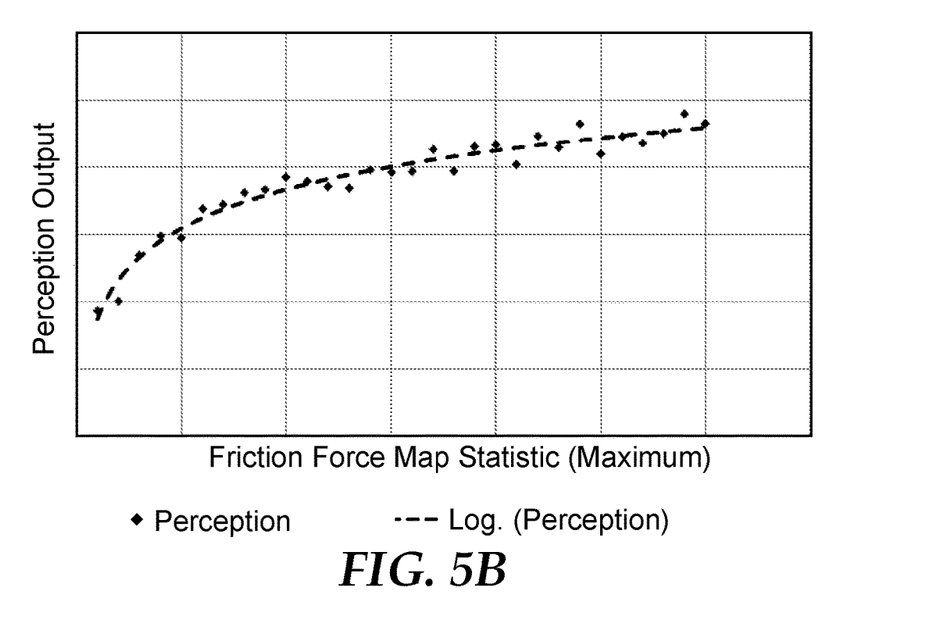
FIG. 5B illustrates the relationship between a friction force map and perception, according to one embodiment.

In some embodiments, existing performance and/or perceptual data of a body-object interface can be combined with friction force map data described herein to provide predictive models regarding the relationship between a friction force map and a user's performance and perception. FIGS. 5A and 5B provide two examples of such relationships between the friction force map and performance and perception. In the example in FIG. 5A, the average friction force at the body-object contact interface is linearly related to human performance (e.g., the maximum pull force can be generated). In the example of FIG. 5B, the friction force map's maximum values can be used to model human comfort that in the example provided is non-linearly related to the friction force map. In other embodiments, such as vibration transference to the body, the friction force map can be used to generate a model that can then be used to predict how successive friction force maps will relate to vibration transference.

Figure 6:
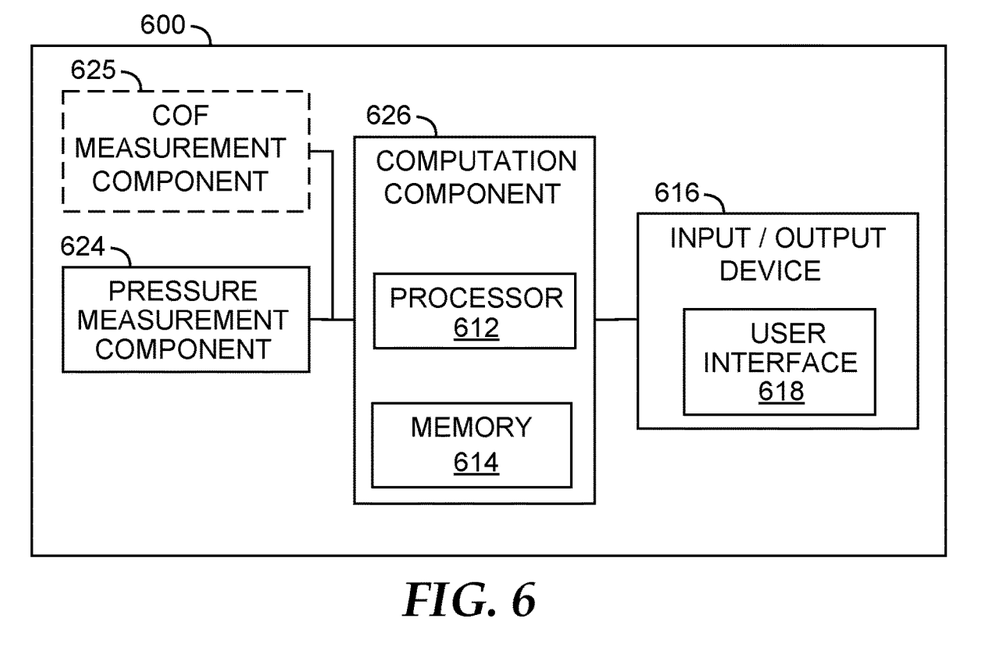
FIG. 6 is a schematic block diagram of a system for optimizing body-object interactions, according to one embodiment.

FIG. 6 illustrates a system 600 for optimizing body-object interactions by implementing, for example, the method 500, according to one embodiment. The system 600 includes a pressure measurement component 624, a computation component 626, and one or more input/output devices 616.

The pressure measurement component 624 is configured to measure pressure values at a contact interface where at least a portion of a body is in physical contact with a surface of an object. The measurement component 624 can be various measurement devices to measure contact pressure. In some embodiments, the pressure measurement component 624 can include, for example, an array of pressure sensors disposed at the contact interface. The pressure sensors can be various types of pressure sensor such as, for example, force collector types that generally use a force collector (e.g., a diaphragm, piston, bourdon tube, or bellows) to measure strain (or deflection) due to applied force (pressure) over an area. A 2D contact pressure map $P(x_i, y_i)$ or a 3D contact pressure map $P(x_i, y_i, z_i)$ can be obtained based on the measured contact pressure values at locations at the contact interface.

In some embodiments, the system 600 may include an optional COF measurement component 625 that is configured to measure coefficient of friction of one or more materials of an object surface. A 2D COF map $COF(x_i, y_i)$ or a 3D COF map $COF(x_i, y_i, z_i)$ at the contact interface can be obtained based on the measured coefficient of friction. It is to be understood that in some embodiments, the coefficient of friction of the materials of the object can be imported from a databased stored in a local/remote memory.

In the embodiment of FIG. 6, the computation component 626 includes a processor 612 and a memory 614. The computation component 626 is functionally connected to the pressure measurement component 624, receives signals related to the measured contact pressure values from the measurement component 624, and generates the contact pressure map $P(x_i, y_i, z_i)$ based on the received signals. The computation component 626 can also generate the COF map $COF(x_i, y_i, z_i)$ based on the coefficient of friction of surface materials that are measured by the optional COF measurement component 625 or imported from a database. The processor 612 can calculate a friction force map $F(x_i, y_i, z_i)$ based on the obtained contact pressure map $P(x_i, y_i, z_i)$ and the obtained coefficient of friction map $COF(x_i, y_i, z_i)$.

The calculated friction force map $F(x_i, y_i, z_i)$ can be stored in the memory 614. In some embodiments, the calculated friction force map $F(x_i, y_i, z_i)$ can be compared to predetermined criteria stored in the memory 614. If the friction force map does not satisfy the predetermined criteria, the contact interface can be adjusted based on comparison in order to optimize body-object interactions. In some embodiments, the obtained friction force map $F(x_i, y_i, z_i)$ can be used to determine whether the object (e.g., a glove, a vest, a respirator, a tool, etc.) is suitable to a body (e.g., a hand, a face, a finger, a leg, a torso, etc) of a specific user.

In some embodiments, the measurement components 624 and/or 625 may be a portable device that can work in field. The measurement components 624 and/or 625 can wirelessly communicate with a remote computing device such as, for example, the computation component 626 by sending and receiving signals. The computation component 626 may be integrated with, for example, a computer, a server, a mobile phone, etc. The computation component 626 can process the received signals, and generate and send information to the input/output device 616 to display thereon.

The memory 614 stores information. In some embodiments, the memory 614 can store instructions for performing the methods or processes described herein. In some embodiments, body or object related data can be pre-stored in the memory 614. For example, geometric characteristics of a body (e.g., a palm side of a hand) or an object, coefficient of friction of one or more materials of the object, predetermined criteria data, etc., can be pre-stored in the memory 614. The obtained contact pressure map $P(x_i, y_i, z_i)$, COF map $COF(x_i, y_i, z_i)$, and friction force map $F(x_i, y_i, z_i)$ can also be stored in the memory 614.

The memory 614 may include any volatile or non-volatile storage elements. Examples may include random access memory (RAM) such as synchronous dynamic random access memory (SDRAM), read-only memory (ROM), non-volatile random access memory (NVRAM), electrically erasable programmable read-only memory (EEPROM), and FLASH memory. Examples may also include hard-disk, magnetic tape, a magnetic or optical data storage media, a compact disk (CD), a digital versatile disk (DVD), a Blu-ray disk, and a holographic data storage media.

The processor 612 may include, for example, one or more general-purpose microprocessors, specially designed processors, application specific integrated circuits (ASIC), field programmable gate arrays (FPGA), a collection of discrete logic, and/or any type of processing device capable of executing the techniques described herein. In some embodiments, the processor 612 (or any other processors described herein) may be described as a computing device. In some embodiments, the memory 614 may be configured to store program instructions (e.g., software instructions) that are executed by the processor 612 to carry out the processes or methods described herein. In other embodiments, the processes or methods described herein may be executed by specifically programmed circuitry of the processor 612. In some embodiments, the processor 612 may thus be configured to execute the techniques for authenticating material samples described herein. The processor 612 (or any other processors described herein) may include one or more processors.

Input/output device 616 may include one or more devices configured to input or output information from or to a user or other device. In some embodiments, the input/output device 616 may present a user interface 618 where a user may control optimizing body and tool interactions. For example, the user interface 618 may include a display screen for presenting visual information to a user. In some embodiments, the display screen can include a touch sensitive display. In some embodiments, a user interface 618 may include one or more different types of devices for presenting information to a user. The user interface 618 may include, for example, any number of visual (e.g., display devices, lights, etc.), audible (e.g., one or more speakers), and/or tactile (e.g., keyboards, touch screens, or mice) feedback devices. In some embodiments, the input/output devices 616 may represent one or more of a display screen (e.g., a liquid crystal display or light emitting diode display) and/or a printer (e.g., a printing device or component for outputting instructions to a printing device). In some embodiments, the input/output device 616 may be configured to accept or receive program instructions (e.g., software instructions) that are executed by the processor 612 to carry out the embodiments described herein.

The system 600 may also include other components and the functions of any of the illustrated components including the processor 612, the memory 614, and the input/output devices 616 may be distributed across multiple components and separate devices such as, for example, computers. The system 600 may be configured as a workstation, desktop computing device, notebook computer, tablet computer, mobile computing device, or any other suitable computing device or collection of computing devices. The system 600 may operate on a local network or be hosted in a Cloud computing environment. The illustrated components of FIG. 6 are shown merely to explain various aspects of the present disclosure and the addition or removal of components would be apparent to one of skill in the art.

Unless otherwise indicated, all numbers expressing quantities or ingredients, measurement of properties and so forth used in the specification and embodiments are to be understood as being modified in all instances by the term "about." Accordingly, unless indicated to the contrary, the numerical parameters set forth in the foregoing specification and attached listing of embodiments can vary depending upon the desired properties sought to be obtained by those skilled in the art utilizing the teachings of the present disclosure. At the very least, and not as an attempt to limit the application of the doctrine of equivalents to the scope of the claimed embodiments, each numerical parameter should at least be construed in light of the number of reported significant digits and by applying ordinary rounding techniques.

Exemplary embodiments of the present disclosure may take on various modifications and alterations without departing from the spirit and scope of the present disclosure. Accordingly, it is to be understood that the embodiments of the present disclosure are not to be limited to the following described exemplary embodiments, but is to be controlled by the limitations set forth in the claims and any equivalents thereof.

Reference throughout this specification to "one embodiment," "certain embodiments," "one or more embodiments," or "an embodiment," whether or not including the term "exemplary" preceding the term "embodiment," means that a particular feature, structure, material, or characteristic described in connection with the embodiment is included in at least one embodiment of the certain exemplary embodiments of the present disclosure. Thus, the appearances of the phrases such as "in one or more embodiments," "in certain embodiments," "in one embodiment," or "in an embodiment" in various places throughout this specification are not necessarily referring to the same embodiment of the certain exemplary embodiments of the present disclosure. Furthermore, the particular features, structures, materials, or characteristics may be combined in any suitable manner in one or more embodiments.

While the specification has described in detail certain exemplary embodiments, it will be appreciated that those skilled in the art, upon attaining an understanding of the foregoing, may readily conceive of alterations to, variations of, and equivalents to these embodiments.

Accordingly, it should be understood that this disclosure is not to be unduly limited to the illustrative embodiments set forth hereinabove. In particular, as used herein, the recitation of numerical ranges by endpoints is intended to include all numbers subsumed within that range (e.g., 1 to 5 includes 1, 1.5, 2, 2.75, 3, 3.80, 4, and 5). In addition, all numbers used herein are assumed to be modified by the term "about". Furthermore, various exemplary embodiments have been described. These and other embodiments are within the scope of the following claims.

What is claimed is:

1. A method comprising:
    obtaining a contact pressure map at a contact interface where at least a portion of a body is in physical contact with a surface of an object, the contact pressure map being a first representation of the contact interface and being expressed as P $(x_i, y_i, z_i)$ where $(x_i, y_i, z_i)$ denotes surface locations of the contact interface;
    obtaining a coefficient of friction (COF) map at the contact interface, the coefficient of friction map being a second representation of the same contact interface and being expressed as COF $(x_i, y_i, z_i)$ where $(x_i, y_i, z_i)$ denotes surface locations of the contact interface and COF $(x_i, y_i, z_i)$ denotes the respective coefficient of friction of one or more materials at the contact interface; and
    calculating, via a processor, a friction force map based on the obtained contact pressure map and the obtained coefficient of friction map, the friction force map being a third representation of the same contact interface and being expressed as $F(x_i, y_i, z_i)$ as a function of the first and second representations P $(x_i, y_i, z_i)$ and COF $(x_i, y_i, z_i)$.

2. The method of claim 1, wherein obtaining the contact pressure map comprises positioning a plurality of sensors at locations on the contact interface, and measuring a set of contact pressure values at the locations.

3. The method of claim 2, wherein obtaining the contact pressure map further comprises converting the set of contact pressure values to the first representation of the contact interface.

4. The method of claim 1, wherein obtaining the coefficient of friction map comprises measuring coefficient of friction for the one or more materials at the contact interface.

5. The method of claim 1, wherein the third representation is obtained by multiplying the first and second representations.

6. The method of claim 1, further comprising adjusting the contact interface.

7. A method comprising:
    obtaining a hand pressure map at a contact interface on a palm side of a glove worn by a hand which is in physical contact with an object, the hand pressure map being a first representation of palmar view of the glove and being expressed as P $(x_i, y_i, z_i)$ where $(x_i, y_i, z_i)$ denotes surface locations of the palm side of the glove;
    obtaining a coefficient of friction (COF) map of one or more materials on the palm side of the glove, and the coefficient of friction map being a second representation of palmar view of the glove and being expressed as COF $(x_i, y_i, z_i)$ where $(x_i, y_i, z_i)$ denotes surface locations of the palm side of the glove and COF (xi, yi, zi) denotes the respective coefficient of friction of the one or more materials on the palm side of the glove; and
    calculating, via a processor, a friction force map based on the obtained hand pressure map and the obtained coefficient of friction map, the friction force map being a third representation of palmar view of the glove and being expressed as F $(x_i, y_i, z_i)$ as a function of the first and second representations P $(x_i, y_i, z_i)$ and COF $(x_i, y_i, z_i)$.

8. The method of claim 7, wherein obtaining the hand pressure map comprises positioning a plurality of sensors at locations on the contact interface, and measuring a set of contact pressure values at the locations.

9. The method of claim 8, wherein obtaining the contact pressure map further comprises converting the set of contact pressure values to the first representation of the contact interface.

10. The method of claim 7, wherein the third representation is obtained by multiplying the first and second representations.

11. The method of claim 7, further comprising adjusting a palm side of the glove.

12. A system comprising:
- a pressure measurement component comprising a plurality of sensors at locations on a contact interface configured to measure an array of contact pressure values at the contact interface where at least a portion of a body is in physical contact with a surface of an object; and
- a computation component functionally connected to the pressure measurement component, configured to receive signals related to the array of contact pressure values from the pressure measurement component, and obtain a contact pressure map based on the received signals, the contact pressure map being a first representation of the contact interface and being expressed as $P(x_i, y_i, z_i)$ where $(x_i, y_i, z_i)$ denotes surface locations of the contact interface, wherein the computation component is further configured to obtain a coefficient of friction (COF) map at the contact interface, the coefficient of friction map being a second representation of the same contact interface and being expressed as $COF(x_i, y_i, z_i)$ where $(x_i, y_i, z_i)$ denotes surface locations of the contact interface and $COF(x_i, y_i, z_i)$ denotes the respective coefficient of friction of one or more materials at the contact interface, and wherein the computation component includes a processor, and the processor is configured to calculate a friction force map based on the obtained contact pressure map and the obtained coefficient of friction map, the friction force map being a third representation of the same contact interface and being expressed as $F(x_i, y_i, z_i)$ as a function of the first and second representations $P(x_i, y_i, z_i)$ and $COF(x_i, y_i, z_i)$.

* * * * *